US00PP26032P3

(12) United States Plant Patent
Zaiger et al.

(10) Patent No.: US PP26,032 P3
(45) Date of Patent: Nov. 3, 2015

(54) INTERSPECIFIC TREE NAMED 'NEWROOT-3'

(50) Latin Name: **Interspecific *Prunus* species**
Varietal Denomination: Newroot-3

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 70 days.

(21) Appl. No.: 13/999,530

(22) Filed: Mar. 7, 2014

(65) Prior Publication Data

US 2015/0257317 P1 Sep. 10, 2015

(51) Int. Cl.
*A01H 5/00* (2006.01)

(52) U.S. Cl.
USPC ..... Plt./180

(58) Field of Classification Search
USPC ..... Plt./180
See application file for complete search history.

*Primary Examiner* — Annette Para

(57) ABSTRACT

A new and distinct variety of interspecific rootstock tree, grown on Handford sandy loam soil with Storie Index rating 95, in USDA Hardiness Zone 9, near Modesto, Calif., with standard commercial nursery practices. Its novelty consist of the following combination of desirable features:

1. The ability to produce rootstock cuttings from dormant hardwood cuttings.
2. Suitability for growing in containers for the home garden market.
3. Reducing the size of mature cherry trees.
4. Increase the number of rootstocks available for cherries.

1 Drawing Sheet

Botanical designation: Interspecific *Prunus* species.
Variety denomination: 'NEWROOT-3'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of rootstocks, plum and cherry trees, which are known to us, and mentioned herein, 'Atlas' Rootstock (U.S. Plant Pat. No. 8,913), 'Viking' Rootstock (U.S. Plant Pat. No. 8,912), 'Amazon' Plum (U.S. Plant Pat. No. 2,043), 'Laroda' Plum (non-patented), 'Queen Ann' Plum (non-patented), 'Royal Dawn' Cherry (U.S. Plant Pat. No. 13,131), 'Newroot-1' Rootstock (U.S. Plant Pat. No. 21,723) and our proprietary selection '82EG198'.

STATEMENT REGARDING FEDERALLY SPONSORED RESEARCH AND DEVELOPMENT

Not applicable.

ORIGIN OF THE VARIETY

The new and distinct variety of interspecific tree, (*Prunus salicina*×*Prunus avium*) was originated by us in our experimental orchard located near Modesto, Calif. as a first generation cross between our proprietary plum selection '82EG198' and 'Royal Dawn' Cherry (U.S. Plant Pat. No. 13,131). The seed parent (82EG198) originated from crosses between 'Laroda' Plum (non-patented), 'Queen Ann' Plum (non-patented) and 'Amazon' Plum (U.S. Plant Pat. No. 2,043). A large number of these seedlings were budded on older trees of 'Nemaguard' Rootstock (non-patented) to induce earlier and larger branch growth to be used for rootstock cuttings to determine the asexual reproduction of these seedlings from cuttings. The seedlings that developed the most desirable rooting ability were selected for propagation to various varieties of cherries (*Prunus avium*). One such selection with desirable rooting ability, which is the present variety, was tested by budding and grafting and found to be compatible with various cherries 'Craig's Crimson) Cherry (U.S. Plant Pat. No. 7,320), 'Royal Rainier' Cherry (U.S. Plant Pat. No. 10,790), and the non-patented cherry varieties 'Van', 'Black Tartarian', 'Stella', 'Bing', 'Lapins', we also budded to approximately 20 proprietary cherry seedling selections. This seedling was selected in 2000 for additional asexual propagation and commercialization.

ASEXUAL REPRODUCTION OF THE VARIETY

Asexual reproduction of the new and distinct variety of interspecific rootstock tree was by dormant hardwood cuttings, as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific rootstock tree (Plum×Cherry), which has vigorous, upright growth and the cuttings from the tree have the ability to develop roots similar to 'Atlas' Rootstock (U.S. Plant Pat. No. 8,913) and 'Viking' Rootstock (U.S. Plant Pat. No. 8,912) when planted directly into the field. The present new variety of interspecific rootstock is further characterized by the rapid rooting of its cuttings, allowing for spring budding of cherries, producing few or any root or trunk suckers. In comparison to its seed parent '82EG198' the fruit of the new variety is small and non-commercial. Compared to its pollen parent 'Royal Dawn' Cherry (U.S. Plant Pat. No. 13,131), the leaves are smaller, more plum like and the fruit is larger in size. In comparison to 'Newroot-1' (U.S. Plant Pat. No. 21,723) the rootstock has slightly more dwarfing effect and is more suited to being grown in containers for the home garden market.

DESCRIPTION OF THE PHOTOGRAPH

The accompanying color photographic illustration shows typical specimens of the foliage and fruit of the present new interspecific rootstock variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 12 year old tree and the colors are as nearly true as is reasonably possible in a color representation of this type.

DESCRIPTION OF THE VARIETY

The following is a detailed botanical description of the new variety of interspecific rootstock tree, its flowers, foliage and fruit, as based on observations of 12 year old specimens grown near Modesto, Calif., with color in accordance with Munsell Book of Color published in 1958.

Tree:

*Size*.—Large, tree pruned severely each winter to induce proper new growth for rootstock cuttings. Average height 3.5 meters. Average width 3.0 meters, varies with different cultural practices.

*Vigor*.—Vigorous. Cut back to 1.5 meters each year to induce new growth for rootstock cuttings each dormant season.

*Form*.—Upright.

*Branching habit*.—New growth from cut back branches have an approximate 40° angle. Branches grow approximately 1.0 to 1.5 meters each season to produce new wood for cuttings.

*Productivity*.—Productive, fruit has no commercial value.

*Bearer*.—Regular.

*Fertility*.—Self sterile.

*Density*.—Dense, numerous branches develop from trees being cutback, this increases density.

*Hardiness*.—Hardy. Tree grown in USDA Hardiness Zone 9. Hardy in all stone fruit growing areas of California.

Trunk:

*Size*.—Medium, circumference 40.6 cm measured 15.2 cm above ground on a 12 year old tree.

*Stocky*.—Medium stocky.

*Texture*.—Medium shaggy, increases with age of tree.

*Color*.—Varies from 10YR 2/2 to 2.5Y 2/2.

Branches:

*Size*.—Medium, average circumference 10.9 cm at 1 meter above ground, varies with tree branches being cut back each dormant season for additional cuttings.

*Surface texture*.—New growth relatively smooth. Mature growth medium rough, roughness increases with age.

*Lenticels*.—Average number 11 in a 25.8 sq cm area. Average length 6.2 mm. Average width 2.3 mm. Color varies from 5YR 5/10 to 7.5YR 5/10.

*Color*.—New growth varies from 5GY 5/8 to 10R 2/6. Old growth varies from 2.5Y 3/2 to 5Y 3/2, varies with age of growth.

Leaves:

*Size*.—Medium. Average length 64.6 mm. Average width 32.3 mm.

*Form*.—Elliptical.

*Apex*.—Acuminate.

*Base*.—Cuneate.

*Margin*.—Doubly serrate.

*Thickness*.—Medium.

*Surface texture*.—Upper surface relatively smooth, only slightly indented over midrib and leaf veins, glabrous. Lower surface relatively smooth, small ridges created by midrib and pinnate venation, glabrous.

*Petiole*.—Average length 11.9 mm. Average width 1.1 mm. Color varies from 2.5GY 5/6 to 5R 3/10. Longitudinally grooved. Surface — very light pubescence.

*Glands*.—Type — globose. Size — small. Average length 0.3 mm. Average diameter 0.3 mm. Number varies from 0 to 3, average number 2. Located primarily on the base of the leaf blade and the upper portion of the petiole. Color varies from 2.5GY 8/6 to 5R 3/10.

*Stipules*.—Present. Average length 6.3 mm. Edges — pectinate. Color varies from 5GY 5/6 to 5R 3/10.

*Color*.—Upper surface varies from 7.5GY 3/4 to 5GY 3/4. Lower surface varies from 5GY 3/4 to 5GY 4/4. Midvein color varies from 10Y 8/4 to 2.5GY 8/6.

Flower buds:

*Size*.—Small to medium. Average length 7.9 mm. Average diameter 4.8 mm.

*Hardiness*.—Hardy with respect all fruit growing areas of California.

*Form*.—Conical, becoming elongated just before opening.

*Pedicel*.—Average length 7.6 mm. Average width 0.6 mm. Color varies from 2.5GY 6/6 to 2.5GY 5/8.

*Color*.—N 9.5/(white).

*Number of buds per spur*.—Average number 16, varies from 12 to 19.

Flowers:

*Blooming period*.—Date of First Bloom Mar. 8, 2013. Date of Petal Fall Mar. 18, 2013, varies slightly with climatic conditions.

*Size*.—Average height 9.5 mm. Average diameter 15.5.

*Petals*.—Normally 5, alternately arranged to sepals. Size — small to medium. Average length 7.4 mm. Average width 6.5 mm. Form — obovate. Arrangement — free. Margin — sinuate. Color N 9.5/(white).

*Sepals*.—Normally 5, alternately arranged to petals. Size — small. Average length 2.7 mm. Average width 2.4 mm. Shape — triangular. Margin — entire. Both upper and lower surface glabrous. Color — upper surface varies from 2.5GY 6/8 to 7.5R 4/10. Lower surface varies from 2.5GY 6/6 to 5R 4/10.

*Stamens*.—Average number per flower 29, varies from 28 to 30. Average filament length 7.0 mm. Filament color N 9.5/(white). Anther color 7.5R 4/10.

*Pollen*.—Self sterile, pollinator required. Color 5Y 7/10.

*Pistil*.—Normally one. Surface glabrous. Average length 9.8 mm. Position of stigma even with anthers. Color varies from 10Y 8/4 to 10Y 8/6.

*Fragrance*.—Heavy.

*Color*.—N 9.5/(white).

*Number flowers per flower bud*.—Average 2, varies from 1 to 4.

*Pedicel*.—Average length 9.2 mm. Average width 0.7 mm. Color varies from 2.5GY 6/6 to 2.5GY 5/8.

Fruit:

*Maturity when described*.—Firm ripe — no commercial value.

*Date of first picking*.—Jun. 20, 2013.

*Size*.—Small. Average diameter axially 35.2 mm. Average transversely in suture plane 36.8 mm. Average weight 31.2 grams, varies slightly with fertility of the soil, amount of thinning and climatic conditions.

*Form*.—Globose.

*Suture*.—Very slightly lipped, extends from base to apex.

*Ventral surface*.—Very slightly lipped.

*Apex*.—Rounded.

*Base*.—Flat.

*Stem cavity*.—Rounded. Average depth 1.8 mm. Average diameter 1.7 mm.

Stem:

*Size*.—Medium to large. Average length 12.5 mm. Average diameter 1.4 mm.

*Color*.—Varies from 2.5GY 6/8 to 2.5GY 5/8.

Flesh:

*Ripens*.—Evenly.

*Texture*.—Firm.

*Fibers*.—Few, small.

*Firmness*.—Firm.

*Aroma*.—Moderate.

*Amydgalin*.—Undetected.

*Eating quality*.—Poor, no commercial value.

*Flavor*.—Slightly tart.

*Juice*.—Heavy amount.

*Brix*.—Average Brix 13.4°, varies slightly with amount of fruit per tree and climatic conditions.

*Color*.—Varies from 2.5Y 8/4 to 2.5Y 8/6.

*Pit cavity*.—Average length 18.0 mm. Average width 14.1 mm. Average depth 5.9 mm. Color 10YR 6/8.

Skin:

*Thickness*.—Medium.

*Surface*.—Smooth.

*Bloom*.—Moderate amount.

*Tendency to crack*.—None.

*Color*.—Ground color varies from 2.5Y 8.5/6 to 2.5Y 8/6. Overspread with 7.5R 2/2 to 7.5R 3/8.

*Tenacity*.—Tenacious to flesh.

*Astringency*.—Slight.

Stone:

*Type*.—Clingstone.

*Size*.—Small to medium. Average length 17.0 mm. Average width 13.1 mm. Average thickness 9.7 mm.

*Form*.—Obovoid.

*Base*.—Flat.

*Apex*.—Rounded.

*Surface*.—Slightly pitted throughout.

*Sides*.—Unequal, one side extending further from suture plane.

*Ridges*.—Very small ridge, extends from base to apex.

*Tendency to split*.—None.

*Color*.—Varies from 7.5YR 4/6 to 7.5YR 4/8 when dry.

Kernel:

*Size*.—Small to medium. Average length 11.6 mm. Average width 8.4 mm. Average depth 5.3 mm.

*Form*.—Obovoid.

*Viability*.—Viable, complete embryo development.

*Skin color*.—Varies from 5Y 9/4 to 7.5Y 9/4.

Use: Rootstock for tree size control, precocious fruiting of cherries and its suitability for growing in containers.

Keeping quality: Not evaluated, fruit of no commercial value.

Shipping quality: Not evaluated, fruit of no commercial value.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific rootstock, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of interspecific rootstock tree, substantially as illustrated and described.

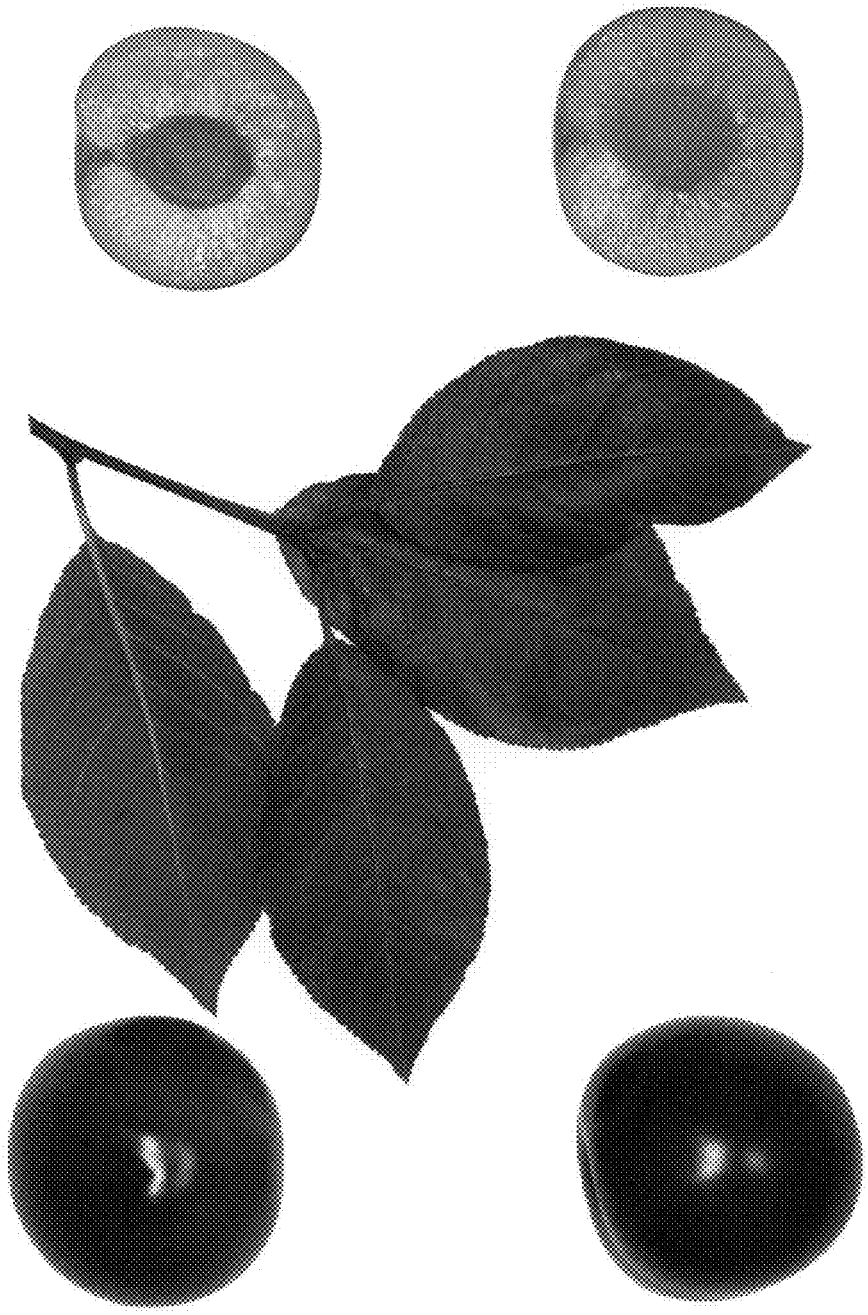

* * * * *